(12) United States Patent  
Gourlay (10) Patent No.: US 10,172,981 B2  
(45) Date of Patent: Jan. 8, 2019

(54) FAT PROCESSING DEVICE

(71) Applicant: BRIGHTWAKE LIMITED, Nottinghamshire (GB)

(72) Inventor: Terence Gourlay, Renfrewshire (GB)

(73) Assignee: Brightwake Limited, Nottingham Nottinghamshire (GB)

( * ) Notice: Subject to any disclaimer, the term of this patent is extended or adjusted under 35 U.S.C. 154(b) by 723 days.

(21) Appl. No.: 14/760,948

(22) PCT Filed: Jan. 6, 2014

(86) PCT No.: PCT/GB2014/050024
§ 371 (c)(1),
(2) Date: Jul. 14, 2015

(87) PCT Pub. No.: WO2014/111688
PCT Pub. Date: Jul. 24, 2014

(65) Prior Publication Data
US 2015/0352266 A1    Dec. 10, 2015

(30) Foreign Application Priority Data

Jan. 15, 2013 (GB) .................................. 1300716.6

(51) Int. Cl.
*A61M 1/00* (2006.01)
(52) U.S. Cl.
CPC ........ *A61M 1/0001* (2013.01); *A61M 1/0094* (2014.02); *A61M 1/0009* (2013.01); *A61M 2202/08* (2013.01)

(58) Field of Classification Search
CPC .............. A61M 1/0001; A61M 1/0009; A61M 1/0094; A61M 2202/08
See application file for complete search history.

(56) References Cited

U.S. PATENT DOCUMENTS

| | | | |
|---|---|---|---|
| 2006/0093527 A1 | 5/2006 | Buss | |
| 2006/0213374 A1 | 9/2006 | Shippert | |
| 2006/0229576 A1* | 10/2006 | Conway | A61F 5/453 604/349 |
| 2008/0319417 A1* | 12/2008 | Quijano | A61M 1/0023 604/522 |

(Continued)

FOREIGN PATENT DOCUMENTS

| | | |
|---|---|---|
| WO | 2011061533 A1 | 5/2011 |
| WO | 2012019103 A2 | 2/2012 |

*Primary Examiner* — Ariana Zimbouski
(74) *Attorney, Agent, or Firm* — Young Basile Hanlon & MacFarlane, P.C.

(57) ABSTRACT

A device for the concentration of a mixture of fatty material and aqueous fluid comprises a chamber for receiving a mixture of fatty material and aqueous fluid, and a body of absorbent material, the chamber being separated from the absorbent material by a barrier member having at least one opening, and a shutter element movable from a closed position, in which said opening is occluded, to an open position, in which said opening permits fluid flow from the chamber to the absorbent material. It has been found that the use of an absorbent material enables fatty material to be concentrated to the required degree in a passive, single vessel process without damage to the fatty tissue. There are also described methods for the use of the device.

25 Claims, 4 Drawing Sheets

(56) References Cited

U.S. PATENT DOCUMENTS

| | | | |
|---|---|---|---|
| 2009/0287190 A1* | 11/2009 | Shippert | A61M 1/0001 604/542 |
| 2009/0306609 A1* | 12/2009 | Blott | A61M 1/0037 604/305 |
| 2010/0112696 A1 | 5/2010 | Min | |
| 2011/0028928 A1* | 2/2011 | Takai | A61F 13/53 604/367 |
| 2011/0106027 A1* | 5/2011 | Vess | A61M 1/0023 604/319 |
| 2012/0068085 A1* | 3/2012 | Cucin | A61B 10/0275 250/492.1 |

* cited by examiner

FAT PROCESSING DEVICE

CROSS REFERENCE TO RELATED APPLICATION

The present application claims priority to Great Britain Patent Application No. 1300716.6, filed Jan. 15, 2013, incorporated herein in its entirety.

TECHNICAL FIELD

This invention relates to devices for and methods of processing fatty material. In particular, this invention relates to devices and methods for use in lipoplasty, and in autologous fat transplantation.

BACKGROUND

Lipoplasty, or liposuction, is a well established method for removing excess fat tissue from specific locations on a patient's body, and generally involves the removal of large quantities of fatty tissue in order to treat conditions such as obesity. Autologous fat injection or transplantation, in which liposuction derived fat tissue is reinjected at a second site on the body, has become increasingly common in both cosmetic and reconstructive surgery to augment tissue or fill body and skin defects. This process is typically concerned with the removal and transfer of much smaller quantities of tissue than are involved in liposuction, often around 50-200 ml at a time.

Autologous fat injection has been used for correcting deformations and/or smoothing skin imperfections in many areas of the body, including the face, thighs, buttocks, breasts and nose. For tissue sculpting, the use of autologous fat is preferable to the use of synthetic materials such as silicone or polyacrylamide gels as it is non toxic and, not being a foreign material, is not rejected by the body.

A number of techniques for removing adipose tissue from the body are known in the art. These include pre-injection of the extraction site with hypotonic saline and hyaluronic acid, or with lidocaine and epinephrine, before removing the fatty tissue under vacuum, the removal of tissue from multiple incision sites to obtain even removal of the tissue (known as "criss-cross"), and the use of high-frequency sound waves to liquefy fat beneath the skin before removal with suction.

In order to reinject autologous fat which has been extracted from a patient, it is necessary to process the extracted fatty material to remove any excess liquid, injected solutions and other impurities. While purifying the fatty material, it is important that the extracted tissue is not damaged as this can affect the success of the graft. For example, it is believed that damaged tissue is one of the causes of injected fat being re-absorbed by the body, removing any beneficial effects which may have been obtained by the transfer.

A number of devices have been developed which seek to combine the extraction of fatty material from the body with purification and reinjection of the same material.

One such device is the LipiVage™ Fat Harvest, Wash and Transfer System, developed by Genesis Biosystems, Inc. In this system, a disposable syringe type device is attached to a low level vacuum and used to extract adipose tissue from the patient into a sterile filtration chamber. Once in the chamber, the extracted fat is mechanically filtered and washed under low pressure, the unwanted components being removed by vacuum into a waste container. The concentrated fat is then transferred into injection syringes, ready for reinjection into the patient.

Another method of autologous fat transplantation is the Coleman system, developed by Dr. S. Coleman, which combines a syringe, cannula and centrifuge. First, a solution of lidocaine, epinephrine and lactated Ringer's solution is injected into the extraction site. Adipose tissue is then removed using a syringe, purified by centrifugation, and reinserted into the patient.

The Viafill™ system is also a disposable, syringe-based system which uses a centrifuge to purify the fatty tissue, with the extraction syringe forming the chamber which is placed in the centrifuge. Reinjection can be carried out through either the harvest syringe, or through a separate transfer device.

Finally, the PureGraft™ system uses vacuum-assisted membrane filtration to remove excess fluids, blood cells and other debris from extracted adipose tissue. Following extraction of the fatty tissue from the patient, a first membrane removes loose blood cells, free lipids, fluid and other debris, and a second membrane directs the flow of the debris and aids in draining of the waste products to a waste bag. Following filtration, the extracted fat is washed with a processing solution, before being reinserted into the patient.

There are a number of disadvantages associated with the products currently available on the market. Many of them rely on centrifugation to purify the fatty tissue; although centrifugation does not generally alter the structure of the adipose tissue, it has been found that the g-forces associated with excessive centrifugation may damage and degrade the adipose tissue, resulting in an unsuccessful transfer of tissue and/or high levels of fat reabsorption by the body. In addition, the devices available are complex, often requiring transfer of the tissue from one vessel to another for purification and/or reinjection. This additional tissue handling can damage the delicate adipose tissue. It also increases the time taken to carry out the procedure, and increases the amount of equipment needed by the practitioner.

SUMMARY

There has now been devised an improved fat processing device, which overcomes or substantially mitigates the above-mentioned and/or other problems associated with the prior art.

According to a first aspect of the invention, there is provided a device for the concentration of a mixture of fatty material and aqueous fluid, the device comprising a chamber for receiving, in use, a mixture of fatty material and aqueous fluid, and a body of absorbent material, the chamber being separated from the absorbent material by a barrier member having at least one opening, and a shutter element movable from a closed position, in which said opening is occluded, to an open position, in which said opening permits fluid flow from the chamber to the absorbent material.

The device according to the invention concentrates lipocytes in the fatty material whilst removing water and dissolved species, through absorption by an absorbent material. This enables the fatty material to be concentrated to the required degree in a passive, single vessel process, without the need for a centrifuge or vacuum which may damage the fatty tissue. In addition, the use of an absorbent material to remove liquid and other unwanted components from a mixture of fatty material and aqueous fluid results in a gelatinous, rather than a liquid, effluent. This both reduces the contamination risk associated with disposing of bodily fluids in a liquid form, and is easier to dispose of.

By "fatty material" is meant, in the context of the invention, fat or adipose tissue which has been extracted from a patient, and may comprise other components in addition to lipids. For example, the extracted fatty material may also comprise whole blood, platelets, plasma, injected solutions such as hypotonic saline, hyaluronic acid, lidocaine and/or epinephrine, etc.

In a preferred embodiment, the device is used to extract the fatty material from a patient prior to concentration of the material. Means for extracting fatty material by liposuction are known in the art, and any suitable means may be used in the present invention. For example, the device may extract fatty material under low pressure or under vacuum, and the fatty material may be extracted via a cannula or needle which is fitted to the device, or which is formed integrally with the device. Prior to extraction of the fatty material, a pre-injection solution may be injected into the extraction site. This solution may comprise, for example, hypotonic saline, hyaluronic acid, lidocaine and/or epinephrine.

After concentration of the fatty material, the device may be used to reinject the fatty material into the patient, for example during autologous fat transplantation. This may be done, for example, by reinjecting the fatty material via a needle or a cannula, and may be done under increased pressure.

Hence, the device of the invention may be used to extract fatty material from a first site on a patient, concentrate the extracted fatty material, and reinject it into a second site on a patient. The use of a single device for all three stages is advantageous as it limits the amount of equipment necessary to carry out autologous fat transplantation, thus reducing costs and simplifying the procedure.

The absorbent material used in the device may be any material which is sufficiently absorbent to remove liquids and other unwanted components from the fatty material. Preferably, the absorbent material is a superabsorbent material.

A superabsorbent material is one which is able to absorb and retain several times its own weight in liquid. Typically, such materials absorb aqueous solutions through hydrogen bonding with water molecules, and may absorb up to 200, 400 or 500 times or more their own weight of liquid.

Amongst the most commonly used superabsorbent materials are polyacrylates, ie salts of polyacrylic acid. For instance, the soldium salt of polyacrylic acid (cross-linked sodium polyacrylate) may be produced by the polymerization of acrylic acid blended with sodium hydroxide in the presence of an initiator.

Other superabsorbent polymers include polyacrylamide copolymer, ethylene maleic anhydride copolymer, cross-linked carboxymethylcellulose, polyvinylalcohol copolymers, cross-linked polyethylene oxide, starch-grafted copolymers of polyacrylonitrile, and others.

Another class of superabsorbent material that may be used in the invention is alginate, ie salts of alginic acid. Such material occurs naturally as a viscous gum that is abundant in the cell walls of brown algae, and commercial forms are extracted from seaweed. Alginic acid is a linear copolymer with homopolymeric blocks of (1-4)-linked β-D-mannuronate and its C-5 epimer α-L-guluronate residues, covalently linked together in different sequences or blocks. Alginates that are particularly suitable for use in the present invention are calcium alginate and sodium alginate.

The volume of absorbent material used in the device is dependent on the nature of the absorbent used and on the quantity of fatty material which is present in the device, but will typically be sufficient to absorb the liquid contained within the fatty material in the chamber.

The absorbent material may typically be located in a second chamber, next to the chamber into which the fatty material is received, with the two chambers being separated by the barrier member. For example, the second chamber may surround the chamber into which the fatty material is received, it may be located above or below the chamber into which the fatty material is received, or it may be located adjacent to the chamber into which the fatty material is received. Preferably the second chamber, containing the absorbent material, surrounds the chamber into which the fatty material is received, providing a large contact area between the fatty material and the absorbent material.

The barrier member is located between the chamber into which the fatty material is received and the absorbent material, and has at least one opening through which the chamber and the absorbent material can be brought into fluid communication.

The barrier member may have more than one opening. For example, the barrier may have two openings, or three openings, or an array of openings. A greater number of openings increases contact between the fatty material in the chamber and the absorbent material, and thus increases the speed with which the fatty material can be concentrated.

The openings may be in any suitable form through which liquid and other unwanted components of the fatty material can pass. For example, the openings may be circular, square or rectangular openings, or may be elongate slots.

The shape of the barrier member is dependent on the shape of the chamber into which the fatty material is received and the relative position of the absorbent material. For example, where the absorbent material is located adjacent to the chamber, the barrier member may be a planar or arcuate barrier between the chamber and the absorbent material. Where the absorbent material surrounds the chamber, the barrier member may be annular.

The shutter element may be located adjacent to, be connected to, or be formed integrally with the barrier member. The shutter element is moveable between two positions, a closed position in which the shutter element occludes the opening(s) in the barrier member, and an open position in which the opening(s) in the barrier member permit the flow of liquid between the chamber and the absorbent material.

The shutter element may be of a corresponding size and shape to the barrier member, having opening(s) which correspond to the opening(s) of the barrier member. Movement of the shutter element relative to the barrier member may then cause the opening(s) of the shutter element and barrier member to move into and out of registration, thus alternately occluding and exposing the opening(s) of the barrier member. Alternatively, the shutter element may be of a corresponding size and shape to the opening(s) of the barrier member, and be moveable alternately across and away from said openings so as to occlude and expose them.

Preferably, the shutter element may be moved between the open and closed positions by the user. This may be effected by means of an actuating member, which causes the shutter to move from an open position to a closed position. For example, where the shutter element has opening(s) which correspond to the opening(s) of the barrier member, the actuating member may cause the opening(s) of the shutter element and barrier member to move into and out of registration. Where the barrier member is an annular barrier member, the actuating member may cause rotation of a corresponding annular shutter member, thus bringing the opening(s) of the shutter element and barrier member into and out of registration.

Preferably, the device further comprises a porous membrane located between the chamber into which the fatty material is received and the absorbent material. The porous membrane may be attached to the barrier member or to the shutter element, or it may form a separate component between the chamber and the barrier member or shutter element, between the barrier member and the shutter element, or between the barrier member or shutter element and the absorbent material.

The use of a porous membrane between the extracted fatty material and the absorbent material allows unwanted liquid and small particles to travel between the chamber and the absorbent material, but prevents the movement of large particles (eg lipocytes) and other cellular material. Larger pore sizes are desirable as they increase the speed with which fluid is absorbed by the absorbent material, but at the same time may result in desired species being lost from the fatty material. Thus, the sizes of the pores preferably correspond to the smallest cell size which it is desired to retain in the fatty material.

Lipocytes are one of the main components of the fatty material extracted from the body, and it is essential that they are retained in the fatty material. They have a size of approximately 70-100 μm. Another species which it is desirable to retain in the fatty material are the platelets, as they help to maintain hemostasis in the body. Platelets have a size of approximately 2-5 μm. The pore size of the porous membrane is thus preferably less than about 70 μm, more preferably less than about 50 μm, more preferably less than about 30 μm, or less than about 15 μm. More preferably, the pore size is less than about 5 μm, or less than about 3 μm. Most preferably, the pore size is between about 1 μm and about 3 μm. Most preferably, the pore size is about 2 μm.

The porous membrane may be any suitable material known in the art. For example, the porous membrane may be a polymeric material. Preferably, the porous membrane is a polycarbonate membrane.

The device according to the invention may be in the form of a syringe. The syringe may be used to extract the fatty material from a first location on a patient, to concentrate the fatty material, and to reinject the concentrated fatty material into the patient at a second location. Fatty material may be extracted from the patient via a cannula, which may be fitted to the syringe or may be formed integrally with the syringe. The syringe plunger may be used to create an area of low pressure inside the syringe, which draws the fatty material inside.

The interior of the syringe may comprise a first chamber for receiving the extracted fatty material, and a second chamber which contains the absorbent material. The two chambers are separated by the barrier member. The barrier member may comprise, for example, a planar or arcuate barrier which divides the interior of the syringe into first and second chambers. Alternatively, the barrier member may be annular, thus creating a first inner chamber and a second, annular chamber between the barrier member and the exterior wall of the syringe. Preferably, the annular chamber may be used to hold the absorbent material while the fatty material is drawn into the inner chamber, though the converse arrangement may also be possible.

Prior to drawing fatty material into the device of the invention, the shutter element may be moved to the closed position such that fluid communication between the chamber for receiving fatty material and the absorbent material is prevented.

Fatty material may be drawn into the device through a cannula or needle, and this may be carried out at low pressure. Low pressure may be applied by, for example, a vacuum or suction pump, or a syringe plunger.

Once the fatty material is in the chamber, the shutter element is moved from the closed position to the open position. This exposes the extracted fatty material to the absorbent material. Liquid and other material is drawn out of the fatty material by the absorbent material, travelling through the one or more openings in the barrier and through the porous membrane, if present. Once the fatty material has reached the necessary concentration, the shutter element is returned to the closed position, occluding the opening(s) in the barrier member and preventing fluid communication between the fatty material and the absorbent material.

The concentrated autologous fatty material may then be reinjected into the patient at a desired location.

The volume of fatty material that is processed using the device according to the invention, particularly in the case of a hand-held syringe-type device, may be in the range 50-200 ml, or 100-150 ml.

Preferably, the length of time for which the fatty material must be exposed to the absorbent material, in order to reach the required degree of concentration, is less than 90 minutes, more preferably less than 60 minutes, or less than 45 minutes, and most preferably less than 30 minutes.

Thus, according to a further aspect of the invention, there is provided a method for concentrating fatty material using the above described device, the method comprising:
a) receiving fatty material in the chamber;
b) moving the shutter element from the closed position to the open position, in order to bring the fatty material into fluid communication with the absorbent material.

According to a further aspect of the invention, there is provided a method for carrying out autologous fat transplantation using the above described device, the method comprising:
a) extracting fatty material from a first location on the patient, so that it is received in the chamber of the device;
b) moving the shutter element from the closed position to the open position, in order to bring the fatty material into fluid communication with the absorbent material;
c) once the fatty material has been concentrated, moving the shutter element from the open position to the closed position;
d) injecting the concentrated fatty material into a second location on the patient.

The fatty material may be extracted from the patient by means of a cannula, which is either fixed to the device or formed integrally with the device.

DESCRIPTION OF THE DRAWINGS

An embodiment of the invention will now be described in more detail, by way of illustration only, with reference to the following drawings, in which.

DETAILED DESCRIPTION OF THE EMBODIMENTS

Figure 1:
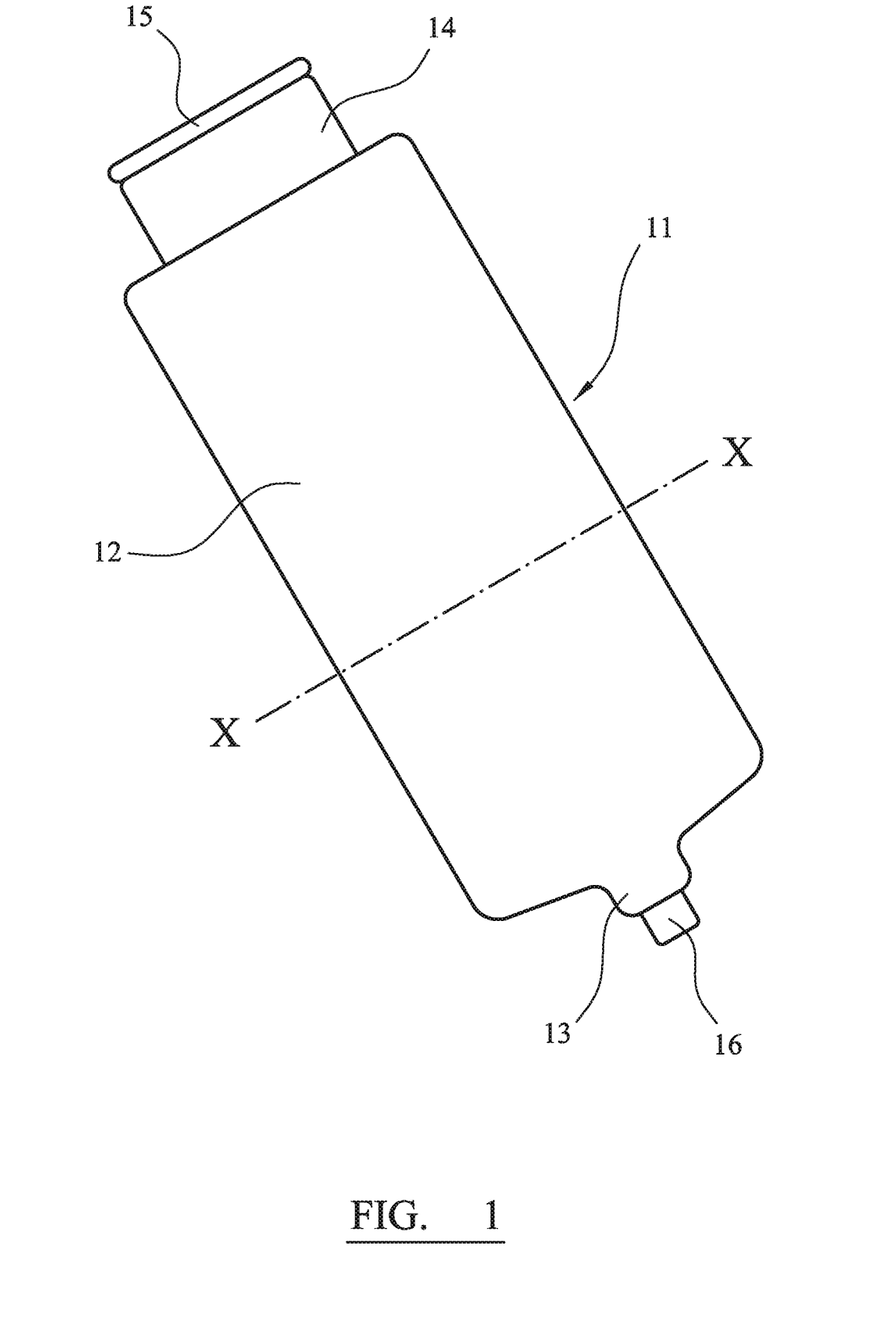
FIG. 1 is a side view of a lipoplasty syringe according to the invention.

Referring first to FIG. 1, a lipoplasty syringe 11 according to the invention is shown. The lipoplasty syringe 11 comprises a tubular housing 12, the proximal end of which tapers to a central opening 13. Also visible in FIG. 1 is an actuating member 14, which is described in more detail below. The actuating member 14 protrudes from the end of the tubular housing 12 distal to the central opening 13, and has a diameter slightly less than the external diameter of the tubular housing 12. The distal end portion of a syringe plunger 15 is also visible in FIG. 1, on top of the actuating member 14.

Figure 2:
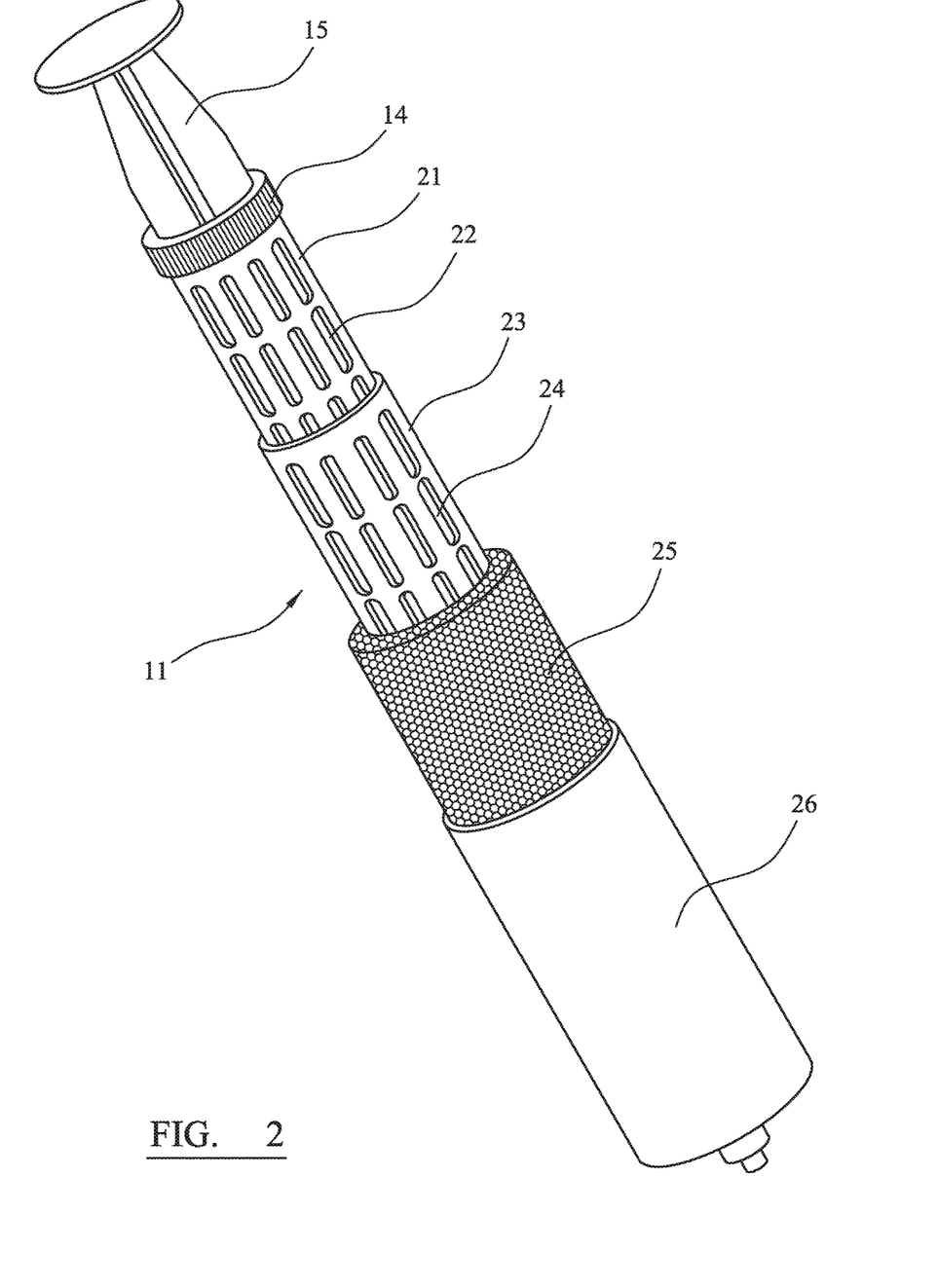
FIG. 2 is a partially disassembled view of the lipoplasty syringe of FIG. 1.

The lipoplasty syringe 11 comprises a number of nested components, which are shown in FIG. 2. Beginning from the centre of the device, a syringe plunger 15 extends through the actuating member 14 and is received within an inner sleeve 21. The inner sleeve 21 is a hollow cylinder, with rows of elongate slots 22 formed in its walls. The inner sleeve is closed at its proximal end, save for an axial tubular spigot 16 that locates in the central opening 13 at the proximal end of the tubular housing 13. In use, a cannula (not shown) is fitted to the spigot 16.

The end of the syringe plunger 15 which is inserted into the inner sleeve 21 is circular, and has a close fit with the interior of the inner sleeve 21. A sealing member (not visible), such as an O-ring or the like, may be present on the end of the syringe plunger 15, such that a seal is formed between the inner wall of the inner sleeve 21 and the end of the syringe plunger 15. In use, the syringe plunger 15 is pressed into, and withdrawn from, the inner sleeve 21, such that when the syringe plunger 15 is withdrawn a fluid-receiving chamber 31 (see FIG. 3) is formed within the interior of the lipoplasty syringe 11.

The actuating member 14 is formed integrally with the distal end of the inner sleeve 21. The actuating member 14 has the form of a ring extending about the circumference of the distal end of the inner sleeve 21, so that, in use, rotation of the actuating member 14 by a user causes rotation of the inner sleeve 21. The actuating member 14 may have a ridged or knurled surface to facilitate such action.

The inner sleeve 21 is received within an outer sleeve 23. The outer sleeve 23 has the form of a hollow cylinder, which is open at both ends and has rows of elongate slots 24 formed in its walls. The slots 24 of the outer sleeve 23 correspond to the slots 22 of the inner sleeve 21, and the two sets of slots 22, 24 can be brought into and out of alignment through rotation of the actuating member 14. The outer sleeve 23 further comprises a porous membrane (not visible in the drawings), which is bonded to the outer surface of the outer sleeve 24 and extends over the elongate slots 24. The porous membrane typically has a pore size of about 2 μm.

The syringe plunger 15, the outer sleeve 23 and the inner sleeve 21 are arranged coaxially within the tubular housing 12. The external diameter of the outer sleeve 23 is somewhat less than the internal diameter of the tubular housing 12, such that there is an annular chamber between them. That annular chamber is filled with a superabsorbent material 25.

In use, when the inner sleeve 21 and the outer sleeve 23 are aligned such that the respective elongate slots 22, 24 are in registration, fluid is able to flow from the fluid-receiving chamber 31, through the porous membrane, to the superabsorbent material 25. When the actuating member 14 is rotated such that the elongate slots 22, 24 are brought out of registration with each other, the flow of fluid in that manner is prevented.

Figure 3:
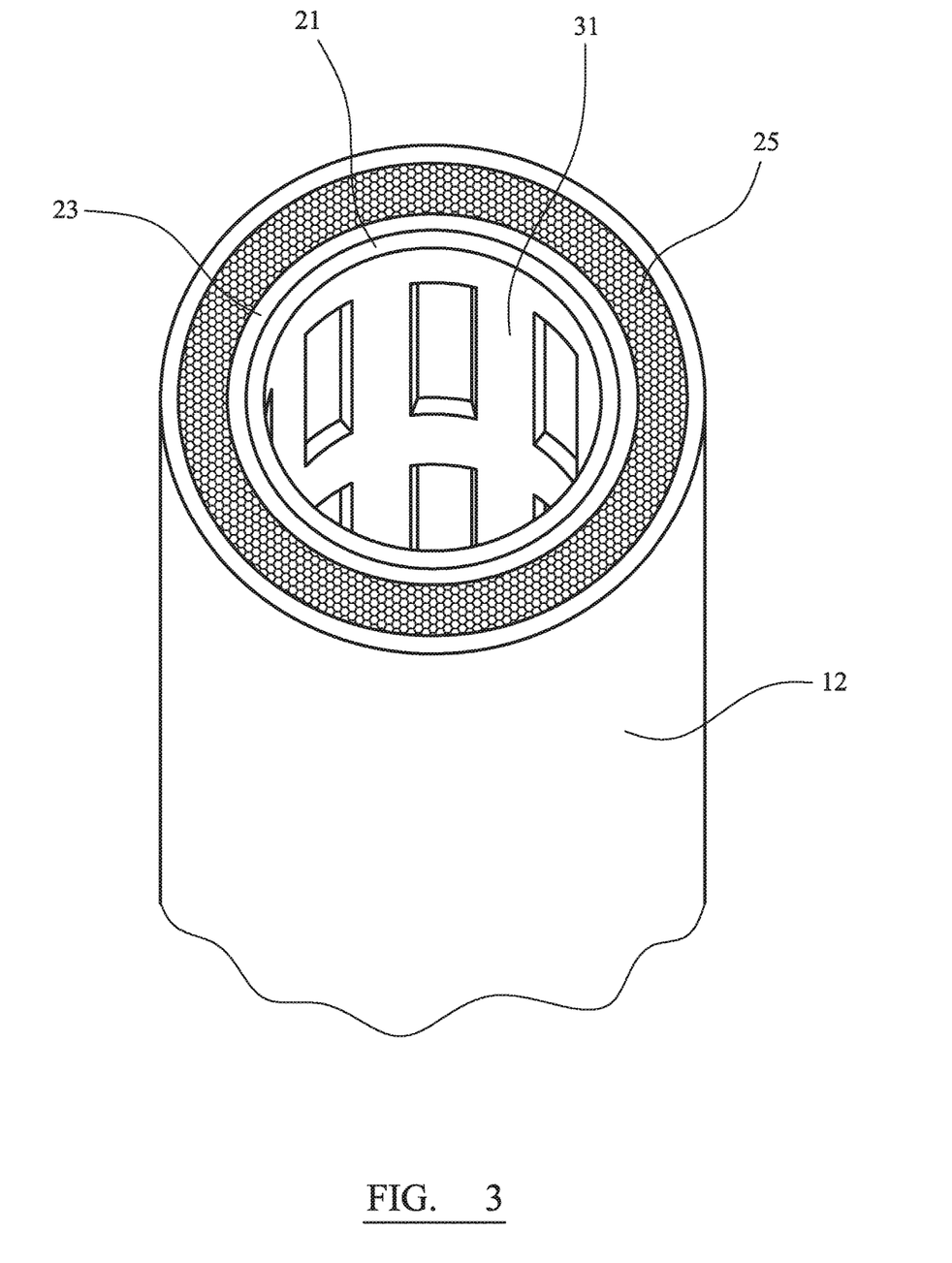
FIG. 3 is a perspective and cross-sectional view of the lipoplasty syringe on line X-X in FIG. 1.

The interior of the lipoplasty syringe 11, with the syringe plunger 15 removed for clarity, is shown in FIG. 3. As can be seen, the tubular housing 12, the superabsorbent material 25, the outer sleeve 23, and the inner sleeve 21 are arranged coaxially and concentrically about the fluid-receiving chamber 31.

Figure 4:
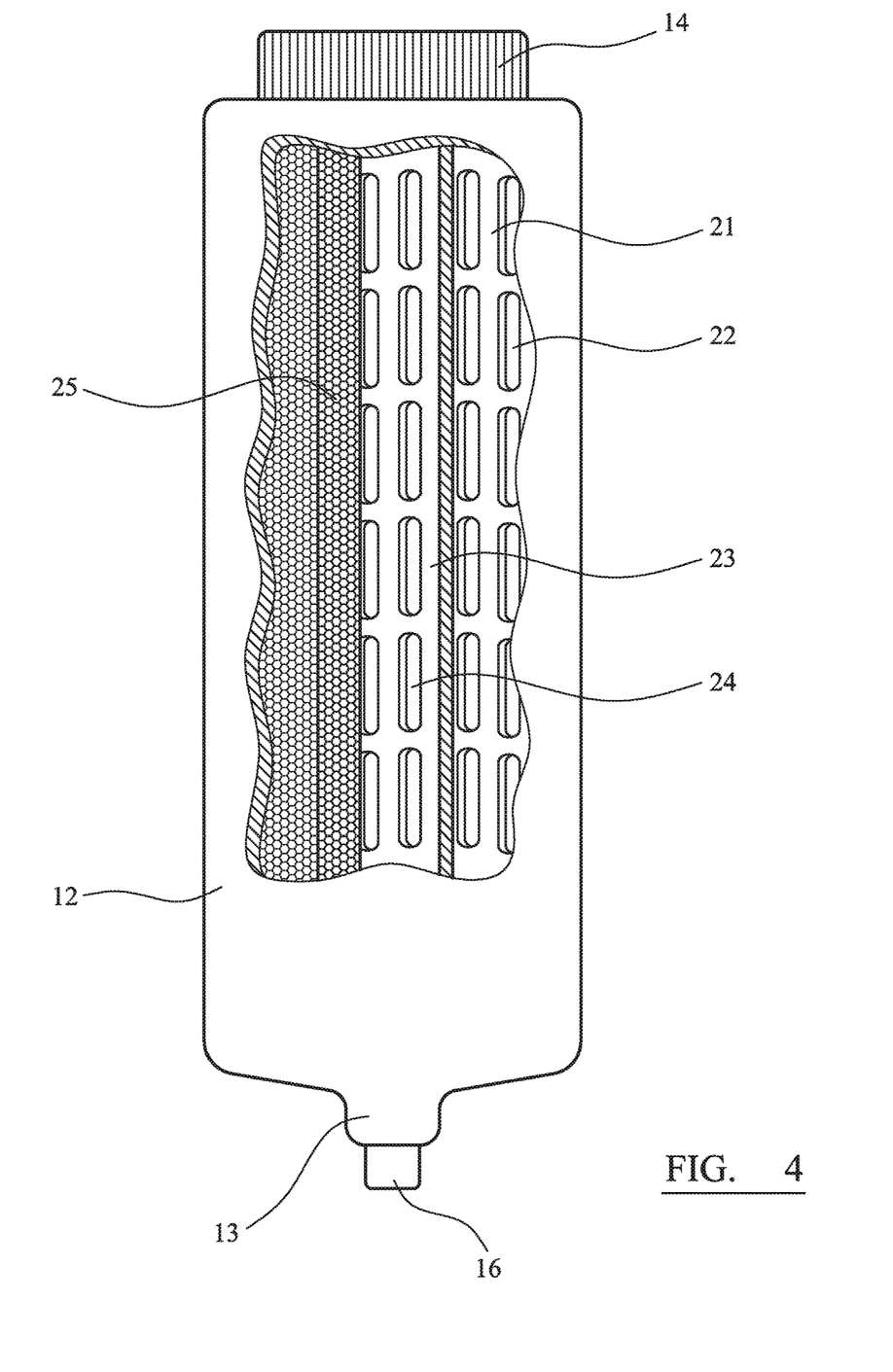
FIG. 4 is a partly cut-away side view of the lipoplasty syringe of FIG. 1.

FIG. 4 shows a side view of the lipoplasty syringe 11, partially cut away to expose the superabsorbent material 25, outer sleeve 23 with elongate slots 24, and inner sleeve 21 with elongate slots 22.

In use, in a lipoplasty procedure, the inner sleeve 21 and the outer sleeve 23 are first arranged (by rotation of the actuating member 14) such that the respective elongate slots 22, 24 are out of alignment with each other. A cannula is fitted to the spigot 16 and, with the syringe plunger fully depressed into the inner sleeve 21, the cannula is inserted into a first location on a patient's body from which it is intended to extract fat. The syringe plunger 15 is then withdrawn, creating reduced pressure in the fluid-receiving chamber 31 and drawing fat (mixed with other fluid) from the patient into the fluid-receiving chamber 31. In some cases, the procedure may involve first charging the device with a fluid (eg hypotonic saline) that is injected into the first location to facilitate the removal of the fat.

Once the required quantity of fatty material has been extracted, the cannula is removed from the patient. The actuating member 14 is rotated in order to bring the slots 22 of the inner sleeve 21 into alignment with the slots 24 of the outer sleeve 23. This exposes the fatty material contained in the fluid-receiving chamber 31 to the superabsorbent material 25, through the porous membrane. The superabsorbent material 25 draws water from the fluid-receiving chamber, the porous membrane preventing the passage of large molecules or cells (eg platelets) into the annular chamber containing the superabsorbent material 25.

Absorption of water from the fatty fluid contained within the fluid-receiving chamber 31 concentrates the extracted fat. Once the fat has been concentrated to the required degree, the actuating member 14 is rotated to move the slots 22 of the inner sleeve 21 out of alignment with the slots 24 of the outer sleeve 23. The concentrated fat may then be reinjected into a second location on the patient's body, by insertion of the cannula into the second location and depressing the syringe plunger 15 to expel the concentrated fat. Alternatively, the concentrated fat may be expelled into a suitable container for storage and subsequent reinjection into the patient.

The invention claimed is:

1. A device for the concentration of a mixture of fatty material and aqueous fluid, the device comprising:
a chamber for receiving, in use, a mixture of fatty material and aqueous fluid, and a body of superabsorbent material, the chamber being separated from the superabsorbent material by a barrier member having at least one opening, and a shutter element movable from a closed position, in which said opening is occluded, to an open position, in which said opening permits fluid flow from the chamber to the superabsorbent material, wherein the device is configured to concentrate the fatty material without a vacuum.

2. The device of claim 1, configured to extract the fatty material from a patient prior to concentration of the fatty material.

3. The device of claim 2, configured to extract the fatty material under low pressure.

4. The device of claim 1, configured to reinject the fatty material into a patient after concentration of the fatty material.

5. The device of claim 1, wherein the superabsorbent material is a polyacrylate.

6. The device of claim 1, wherein the superabsorbent material is an alginate.

7. The device of claim 1, wherein the superabsorbent material is located in a second chamber.

8. The device of claim 7, wherein the second chamber surrounds the chamber into which the fatty material is received.

9. The device of claim 8, wherein the barrier member is annular.

10. The device of claim 1, wherein the barrier member has an array of openings.

11. The device of claim 1, wherein the at least one opening is in the form of one or more elongate slots.

12. The device of claim 1, wherein the shutter element is adjacent to the barrier member.

13. The device of claim 1, wherein the shutter element has at least one opening, each opening corresponding to a respective opening of the barrier member.

14. The device of claim 1, further comprising an actuating member, said actuating member causing the shutter to move from the closed position to the open position, and from the open position to the closed position.

15. The device of claim 14, wherein the shutter element has at least one opening, each opening corresponding to a respective opening of the barrier member, and wherein the actuating member causes the corresponding openings on the shutter element and barrier member to move into and out of registration.

16. The device of claim 1, which further comprises a porous membrane located between the chamber into which the fatty material is received, and the superabsorbent material.

17. The device of claim 16, wherein a pore size of the porous membrane is less than about 5 μm.

18. The device of claim 17, wherein the pore size of the porous membrane is less than about 3 μm.

19. The device of claim 18, wherein the pore size of the porous membrane is about 2 μm.

20. The device of claim 16, wherein the porous membrane is a polycarbonate membrane.

21. The device of claim 1 which is in the form of a syringe.

22. The device of claim 1, which can process approximately 50-200 ml of fatty material.

23. A method for concentrating fatty material using the device of claim 1, the method comprising:
   a) receiving fatty material in the chamber;
   b) moving the shutter element from the closed position to the open position, in order to bring the fatty material into fluid communication with the superabsorbent material.

24. A method for carrying out autologous fat transplantation using the device of claim 1, the method comprising:
   a) extracting fatty material from a first location on the patient, so that it is received in the chamber of the device;
   b) moving the shutter element from the closed position to the open position, in order to bring the fatty material into fluid communication with the superabsorbent material;
   c) once the fatty material has been concentrated, moving the shutter element from the open position to the closed position;
   d) injecting the concentrated fatty material into a second location on the patient.

25. The method of claim 24, wherein the fatty material is extracted from the patient via a cannula.

* * * * *